(12) United States Patent
Yabuki et al.

(10) Patent No.: US 9,170,243 B2
(45) Date of Patent: Oct. 27, 2015

(54) METHOD FOR DETERMINING ODOR WHEN USING A SELF-TANNING AGENT

(71) Applicants: Masayuki Yabuki, Tokyo (JP); Miki Takahashi, Tokyo (JP)

(72) Inventors: Masayuki Yabuki, Tokyo (JP); Miki Takahashi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/761,441

(22) Filed: Feb. 7, 2013

(65) Prior Publication Data

US 2013/0210159 A1      Aug. 15, 2013

Related U.S. Application Data

(60) Provisional application No. 61/596,965, filed on Feb. 9, 2012.

(51) Int. Cl.
| | |
|---|---|
| *G01N 33/497* | (2006.01) |
| *G01N 33/50* | (2006.01) |
| *G01N 31/00* | (2006.01) |
| *G01N 30/72* | (2006.01) |
| *C07D 241/12* | (2006.01) |
| *G01N 30/88* | (2006.01) |

(52) U.S. Cl.
CPC .............. *G01N 31/00* (2013.01); *C07D 241/12* (2013.01); *G01N 30/7206* (2013.01); *G01N 2030/8813* (2013.01); *Y10T 436/147777* (2015.01)

(58) Field of Classification Search
None
See application file for complete search history.

(56) References Cited

PUBLICATIONS

Lloyd et al. (2001) Journal of Investigative Dermatology 117: 740-742.*
Hindenlang, D.M., et al., "Reducing Odiferous Volatiles with Zeolites", Cosmetics & Toiletries, vol. 123, No. 7, Jul. 2008.
Nursten, H.E., "Recent Developments in Studies of the Maillard Reaction", Food Chemistry 6 (1980-81) 263-277.
Waller, G.R. ed., et al., "The Maillard Reaction in Foods and Nutrition", ACS Symposium Series, vol. 215, Chapter 12, pp. 185-286, Apr. 29, 1983.

* cited by examiner

*Primary Examiner* — Michael Pak
(74) *Attorney, Agent, or Firm* — Frost Brown Todd LLC (57) ABSTRACT

A method for evaluating an odor generated when using a self-tanning agent, wherein at least one compound selected from pyrazine compounds represented by the following general formula (1) is used as an indicator substance:

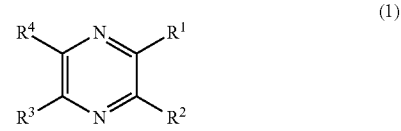

(1)

wherein $R^1$ represents a methyl group, an ethyl group or an acetyl group, and $R^2$, $R^3$ and $R^4$ independently represent a hydrogen atom or a methyl group.

2 Claims, 4 Drawing Sheets

METHOD FOR DETERMINING ODOR WHEN USING A SELF-TANNING AGENT

TECHNICAL FIELD

The present invention relates to a method for evaluating odor generated when a self-tanning agent (sunless tanning agent) is applied to the skin, and a method for evaluating the efficacy of an odor-decreasing agent targeting the odor.

BACKGROUND ART

In North America or Europe, there is a tendency that brown skin, which has been healthily tanned, is preferred. However, there is a concern that a suntan resulting from sunbathing or a tanning machine can cause cutaneous cancer or freckles by the effect of ultraviolet rays. Thus, a self-tanning agent is favorably used, which is capable of rendering the color of the skin a natural and healthy brown color similar to the color based on a suntan, without being affected by ultraviolet rays.

The self-tanning agent is also referred to as a sunless tanning agent, and is a skin cosmetic for coloring the skin. In many cases, as a component thereof for turning the skin into a brown color, dihydroxyacetone (DHA) is used alone, or is used together with erythrulose or some other components. When dihydroxyacetone is used together with erythrulose, usually, dihydroxyacetone is mixed at a higher concentration than erythrulose. By effect of these components, the stratum corneum of the skin becomes colored brown. It is said that this coloring is generally advanced by a browning reaction, and is caused by the generation of a polymer having a structure similar to that of a brown colorant called melanoidin. However, details of the reaction mechanism thereof have hardly been elucidated. For reference, in the field of food chemistry, a browning reaction is also called Maillard reaction. The browning reaction generally means a reaction through which a nitrogen-containing compound, such as an amino acid or a protein, and a reducing sugar are polymerized to generate melanoidin.

Sometimes, when a self-tanning agent is used, a distinct unpleasant odor is generated, and this causes a problem. Hitherto, however, little research and few reports have been made about unpleasant odors generated when this self-tanning agent is used. Thus, improvement of the technique is desired.

D. M. Hindenlang and M. E. McDonnell, Cosmetics & Toiletries magazine, 2008, Vol. 123, No. 7, p. 67-74, states that it is difficult to mask the odor generated when a self-tanning agent is used. However, this document does not have a description about the causative substance of the odor.

In the field of food, research has been made about the Maillard reaction, which is generated by a reducing sugar and an amino acid. H. E. Nursten, Food Chemistry, 1981, 6(3), 263-277, states that through a Maillard reaction between a dicarbonyl compound and an amino acid, a pyrazine compound is generated. However, the document does not have a description about a relationship between the pyrazine compound and any self-tanning agent. S. Fors, Sensory Properties of Volatile Maillard Reaction Products and Related Compounds, "The Maillard Reaction in Foods and Nutrition" (ACS Symposium Series, Vol. 215), Chapter 12, pp. 185-286 Publication Date (Print): Apr. 29, 1983, describes odors obtained by Maillard reaction in the field of food chemistry. In this document, it is stated that a pyrazine compound emits a pleasant odor by which a food is characterized. For example, 2,6-dimethylpyrazine has a "sweet, fried, resembling fried potatoes, nutty, and roasted" odor. However, this document does not refer to a relationship between the pyrazine compound and a self-tanning agent.

As described above, a sufficient investigation has not yet been made about compounds generated by a reaction between a self-tanning agent and the skin. Moreover, volatile components known as a product from Maillard reaction in the field of food have been recognized as favorable and pleasant odor components, and been conceived to be irrelevant to the unpleasant odor generated by a reaction between a self-tanning agent and the skin.

SUMMARY

The invention provides a method for evaluating an odor generated when using a self-tanning agent, wherein at least one compound selected from pyrazine compounds represented by the following general formula (1), which may be hereinafter referred to as a "pyrazine compound (1)", is used as an indicator:

wherein $R^1$ represents a methyl group, an ethyl group or an acetyl group, and $R^2$, $R^3$ and $R^4$ independently represent a hydrogen atom or a methyl group.

The invention further provides a method for evaluating an odor-decreasing agent for a self-tanning agent, or a self-tanning agent to which this odor-decreasing agent is blended, wherein at least one compound selected from pyrazine compounds represented by the general formula (1) is used as an indicator.

DESCRIPTION OF EMBODIMENTS

A self-tanning agent (sunless tanning agent) targeted by the invention contains dihydroxyacetone, and may further contain erythrulose.

Hitherto, the evaluation of an unpleasant odor generated by applying a self-tanning agent to the skin (the odor may be referred to as "tanning odor" hereinafter), and the evaluation of the efficacy of an odor-decreasing agent targeting tanning odor depend on a sensory evaluation test in which the self-tanning agent is actually applied to the skin and then an odor generated from the skin is smelled and judged. However, in the sensory evaluation test, wherein the evaluation criteria for the evaluation is unclear, there is large room in which the evaluator's subjective judgment produces an influence. Thus, the test has problems that quantitative evaluation cannot be easily made and further the result lacks objectivity.

The inventors investigated an unpleasant odor generated when a self-tanning agent is used, which is pointed out in D. M. Hindenlang and M. E. McDonnell, Cosmetics & Toiletries magazine, 2008, Vol. 123, No. 7, p. 67-74. As a result, it was found that the odor experienced by a person to be unpleasant after using a self-tanning agent is an odor expressed an earthy, burnt sugar, and the like. It was further found out that this earthy odor is an odor recognized to be an unpleasant odor, in particular, from the initial stage to the middle stage of the reaction, and is also an odor recognized frequently when the concentration of dihydroxyacetone in the self-tanning agent is particularly low (about a concentration of 1 to 3% by mass).

Moreover, the inventors also made the cutaneous keratin collected from a human being to react with dihydroxyacetone in vitro, and then found that lower aldehydes, lower fatty acids, furans, pyrans, and pyrazines may be generated as volatile substances generated by the reaction between the skin of a human being and dihydroxyacetone and/or erythrulose.

Further, the inventors developed a method capable of analyzing easily odor components generated when a tanning agent is applied to the skin of a human being. The inventors used this method to analyze tanning odor and found that pyrazines are not detected from skin to which no self-tanning agent is applied while pyrazines are detected in the state that a self-tanning agent is applied thereto and tanning odor is generated. In addition, the inventors found that the odor of the pyrazine compound resembles tanning odor, the compound largely contributes, in particular, to the earthy odor, and the pyrazine compound is a typical component which constitutes/creates tanning odor.

The inventors further found that a group of pyrazine compounds close to each other in structure, that is, any pyrazine compound (1) can be used as an objective indicator for evaluating tanning odor quantitatively, and then developed the method of the invention in which this indicator is used to make it possible to evaluate whether or not tanning odor is generated, and whether tanning odor is strong or weak, and further evaluate the efficacy of an odor-decreasing agent targeting tanning odor objectively and quantitatively.

Pyrazine Compound (1) Used as an Indicator

The pyrazine compound (1) used as an indicator in the invention is a compound illustrated below:

wherein $R^1$ represents a methyl group, an ethyl group or an acetyl group, and $R^2$, $R^3$ and $R^4$ independently represent a hydrogen atom or a methyl group. One or more compounds selected from these compounds are used as an indicator. It is preferred to use the compounds wherein at least one of $R^1$ to $R^4$ is an alkyl group. Examples thereof include 2-methylpyrazine, 2,6-dimethylpyrazine, 2,5-dimethylpyrazine, 2-ethyl-6-methylpyrazine, 2-acetyl-3-methylpyrazine, 2,3,6-trimethylpyrazine, and 2-acetyl-3,5-dimethylpyrazine. It is particularly preferred to use 2,6-dimethylpyrazine, or 2,5-dimethylpyrazine.

These compounds represent a group of compounds extremely similar to each other in chemical structure which mainly includes compounds that was found as causative substances of tanning odor by the inventors. Examples of these compounds include 2-methylpyrazine, 2,6-dimethylpyrazine, 2,5-dimethylpyrazine, 2-ethyl-6-methylpyrazine, 2-acetyl-3-methylpyrazine, 2,3,6-trimethylpyrazine, and 2-acetyl-3,5-dimethylpyrazine. Frequently detected components are, in particular, 2,6-dimethylpyrazine and 2,5-dimethylpyrazine. These pyrazine compounds are compounds well-known as flavors for food. However, it has not yet been reported that any one of the compounds is a component that constitutes/creates the tanning odor.

Many of the pyrazine compounds (I) are commercially available. Thus, by using a reagent having a predetermined quality, tanning odor can be objectively evaluated. In this point also, the pyrazine compounds are each suitable as an indicator.

Method for Evaluating Tanning Odor

According to the invention, the degree of tanning odor can be evaluated by use of a pyrazine compound (1) as an indicator. The method for using a pyrazine compound (1) as an indicator for evaluating tanning odor is not particularly limited. Thus, it is advisable to use the compound in a state that the compound is adapted to any one of various known methods.

The method of the invention for evaluating tanning odor preferably includes the following steps (a), (b) and (c):

step (a) of bringing the stratum corneum of a human being, keratin obtained from the skin of a human being, or a hydrolyzate of any one of the above two into contact with the self-tanning agent, thereby advancing a reaction therebetween, step (b) of collecting volatile substances generated by the reaction, and step (c) of measuring the pyrazine compound (1) that is contained in the collected volatile substances, and evaluating the odor based on a result of the measurement.

About Step (a):

First, a self-tanning agent is applied to skin of a human being to start a coloring reaction. Alternatively, separately, it may mix a keratin such as cutaneous keratin, collected from a human being, or a hydrolyzate thereof with a self-tanning agent to cause a coloring reaction. When the keratin collected from the human being is mixed with dihydroxyacetone or the self-tanning agent to advance the reaction, it is preferred to employ a method by using, for example, a keratin smoother to collect keratin in a powdery state from a heel or some other parts.

When the cutaneous keratin is mixed with the self-tanning agent to conduct the coloring reaction, it is preferred to conduct the reaction at a temperature from room temperature to about 50° C. The effect of humidity is small; thus, it is preferred to conduct the reaction at a relative humidity of 5 to 100%. More specifically, the reaction may be conducted at a temperature of 20 to 40° C. and a relative humidity of 5 to 60%, for example, at 37° C. and a relative humidity of 40%. The blend ratio between the keratin and the self-tanning agent can be varied in accordance with the concentration of dihydroxyacetone contained in the self-tanning agent. When the present system is subjected to sensory evaluation and/or volatile substances therefrom are analyzed, the ratio of the keratin to dihydroxyacetone is preferably from 1:750 to 1000:1, more preferably from 1:40 to 50:1. For example, to 0.1 to 2 g of the self-tanning agent containing dihydroxyacetone in a proportion of 2%, it is preferred to mix 1 to 100 mg of the keratin. In the case of the self-tanning agent containing dihydroxyacetone in the proportion of 2% by mass, it is more preferred to mix 5 to 20 mg of the keratin (the ratio of the keratin to dihydroxyacetone is from 2:1 to 1:2) into 0.5 g of the self-tanning agent. The resultant mixture may be applied onto a medicine paper piece to advance the reaction, or may be put into a glass tube (bottle) to advance the reaction therein. When the reaction is conducted on the medicine paper piece, this paper-piece system is easily subjected to sensory evaluation.

About Step (b):

The method for collecting an odor generated by the reaction is not particularly limited, and includes, for example, a method by using a resin or some other materials that can collect volatile substances to collect the odor. When the self-tanning agent has been applied directly to the skin of a human being, for example, a resin or some other materials that is capable of collecting volatile substances is set onto the inside of a jacket (sleeve) or some other materials that are made of Teflon (®) and can cover the forearm. By putting the forearm to which the self-tanning agent is applied through the jacket or the other, volatile substances volatilized from the arm can be collected.

Examples of the resin include 2,6-diphenyl-p-phenylene oxide (Tenax TA®, manufactured by GL Science Inc.), silica gel, activated carbon, polydimethylsiloxane, divinylbenzene, carboxen, and a carbon molecular sieve; and any combination of two or more thereof.

When the keratin collected from the human being, or keratin that originates from a human being and is commercially available as a reagent is mixed with the self-tanning agent, the mixing is attained in, for example, a glass tube so that volatile substances can be generated in a head space inside the glass tube. A method for collecting the volatile substances includes, for example, inserting a tool for a solid phase micro extraction (a tool in which the surface of a wire is coated with a colleting agent) into the head space of a glass tube (bottle), and then allowing the glass tube to stand still, or a method introducing the air which is odorless into the glass tube which is a glass tube filled with the Tenax TA® resin, so as to pass the gas in the head space through the inside of this glass tube, thereby concentrating the gas on the Tenax TA resin.

About Step (c):

The measurement of the pyrazine compound (1) is preferably subjected to analysis by using a gas chromatography-mass spectrometer (GC-MS) or some other instrument to determine the composition of the volatile substances collected in step (b), and the quantities of the substances. This method makes it possible to make a direct analysis of the components volatilized from the skin and to measure the presence or absence of the pyrazine compound (1) or the presence amount thereof.

When the amount of the pyrazine compound (1) contained in tanning odor is measured by means of the GC-MS, it is advisable to use the pyrazine compound (1) beforehand as a standard substance to prepare a calibration curve, use this calibration curve to identify a peak of the pyrazine compound (1) contained in the sample collected from the skin of human being when the self-tanning agent is used, and then measure the amount thereof.

In the evaluation of the odor based on the pyrazine compound (1), a person may directly smell the odor generated by the reaction to evaluate the presence or the absence of the pyrazine by sensory evaluation. In this case, the method for evaluating tanning odor includes a step (c') described below instead of the steps (b) and (c). In other words, the evaluating method in this case includes the steps (a) and (c'):

the step (c') of smelling volatile substances generated by the reaction, comparing the odor sensed by the swelling with the odor of the pyrazine compound (1) as the indicator, and evaluating the sensed odor based on a result of the comparison.

When the sensory evaluation is made, it is advisable to dilute the pyrazine compound (1) beforehand into several levels of concentration to prepare respective odor standard samples at the resultant concentrations, smell the odor from the skin of a human being when the self-tanning agent is applied, and compare the smelled odor with the odors of the standard samples to evaluate the amount of the pyrazine compound (1).

As described above, the evaluating method of the invention may be used for any one of instrumental analysis and sensory evaluation. According to, in particular, instrumental analysis, subjectivity can be excluded from the result of the evaluation by expressing each measured value by the amount of the pyrazine compound (1), Thus, quantitative evaluation can be attained.

Method for Evaluating an Odor-Decreasing Effect Targeting Tanning Odor

Furthermore, according to the invention, a pyrazine compound (1) is used as an indicator to make it possible to evaluate an odor-decreasing effect of an odor-decreasing agent for a self-tanning agent, or a self-tanning agent to which this odor-decreasing agent is blended.

The odor-decreasing agent (also includes a self-tanning agent to which this odor-decreasing agent is blended) to be evaluated may have an action mechanism of any type, such as a type of decomposing or changing an odor component to a derivative emitting no odor, or a type of masking tanning odor. The method for using the pyrazine compound (1) as an indicator for evaluating the efficacy of the odor-decreasing agent is not particularly limited. Thus, the compound may be used in the state of being adapted to the action mechanism of the odor-decreasing agent and evaluation method.

When the odor-decreasing agent is of a type of decomposing an odor component or deriving the component to another compound to decrease tanning odor, or a type of restraining the volatilization of an odor component, it is preferred to prepare a calibration curve of the pyrazine compound (1) beforehand, and use this calibration curve to make an instrumental analysis. In this case, the method for evaluating the odor-decreasing agent preferably includes the following steps (d) and (e):

step (d) of bringing the self-tanning agent odor-decreasing agent, or the self-tanning agent to which this odor-decreasing agent is blended, into contact with the pyrazine compound (1), the amount of this compound being beforehand measured, and step (e) of collecting the pyrazine compound (1) and measuring the pyrazine compound after step (d), thereby calculating the reduction amount of the pyrazine compound from the amount of pyrazine compound used in step (d), and then evaluating an odor-decreasing effect of the agent based on the result obtained by the calculation.

About Step (d):

The pyrazine compound (1) may be used alone, or may be used in the state of being prepared into a composition suitable for practical use, such as storage or use in an evaluating test. The composition may be prepared by mixing into the compound, an additive such as another component including a solvent for dissolution or dilution, a stabilizer, an antibacterial agent, a surfactant, an antioxidant, a perfume, a plant extract, or the like. In order to compare the value of the used amount of pyrazine compound (1) with a value measured in step (e), it is necessary to measure this used amount before use.

About Step (e):

In step (e), the pyrazine compound (1) can be collected in the same way as in step (b).

In the measurement of the pyrazine compound (1) in steps (d) and (e), the degree of the odor-decreasing effect can be directly grasped as the numerical data of the decreased amount. It is therefore preferred to take the measurement by using an instrument such as a GC-MC, in the same manner as in step (c) in the tanning-odor-evaluating method.

When the odor-decreasing agent is of a type of masking tanning odor, or when the effect of the odor-decreasing agent is desired to be simply and easily evaluated without using any instrument, it is advisable to dilute the pyrazine compound (1) beforehand into several levels to prepare respective odor standard samples at the resultant concentrations, and compare the odor of the pyrazine compound (1) to which the odor-decreasing agent is added with the odors of the standard samples to evaluate the masking effect according to the sensory evaluation. In this case, the method for evaluating the odor-decreasing agent preferably includes the following steps (d') and (e'):

step (d') of bringing the self-tanning agent odor-decreasing agent, or the self-tanning agent to which this odor-decreasing agent is blended, into contact with the pyrazine compound (1), the intensity of the odor of this compound being beforehand subjected to sensory evaluation, and step (e') of subjecting the intensity of the odor of the pyrazine compound (1) again to the sensory evaluation after step (d'), comparing the intensity obtained by the sensory evaluation with the intensity of the odor of the pyrazine compound (1) used in step (d'), and then evaluating the odor-decreasing effect of the agent based on the result obtained by the comparison.

When the odor-decreasing agent is of a type of restraining the generation itself of an odor component, the method includes the following step (d'') instead of step (d) or (d'):

step (d'') of adding the odor-decreasing agent to dihydroxyacetone or the self-tanning agent to which no odor-decreasing agent is blended, and bringing the resultant into contact with skin or keratin originating from skin, thereby advancing a reaction therebetween.

In the evaluating step conducted after step (d''), quantitative evaluation may be made as in step (e), or sensory evaluation may be made as in step (e').

When an appropriate agent is selected from odor-decreasing agents, it is advisable to evaluate the respective odor-decreasing effects of the agents by the above-mentioned evaluating method, and then select an agent having a high odor-decreasing rate.

EXAMPLES

Test Example 1

Analysis of Volatile Substances Generated by Reaction Between Dihydroxyacetone and Cutaneous Keratin Volatile substances generated by the reaction between dihydroxyacetone and cutaneous keratin were analyzed.

A subject (healthy Japanese man) was requested not to use any cream or the like on his heels on the day before the keratin-collection. One of the heels was sufficiently washed with tepid water, and then sufficiently dried. In this state, the subject was requested to use a commercially available keratin smoother (motorized heel smoother, Panasonic ES2502PP) to collect old keratin (powdery form) from the heel. After the collection, the keratin was put into a glass vessel, and the vessel without being capped was allowed to stand still in a drying machine (temperature: 50° C.) overnight. In this way, almost odorless and white powder that was dehydrated was obtained. This dry keratin was stored in a refrigerator in the state that the glass tube was capped except when the keratin was used.

Inside the glass vessel (20 mL), 10 mg of the dry keratin was mixed with 0.1 mL of an aqueous solution of dihydroxyacetone (10% v/v). The upper part of the vessel thereof was capped with a rubber septum. While the vessel was heated (at 50° C.), the vessel was stored for 5 days. As a result, the keratin was changed to brown, and a strong reaction odor was generated. A solid phase micro extraction (SPME) fiber was stuck into the rubber septum, and the generated volatile components were collected. The components were then subjected to GC-MS analysis. The result is shown in FIG. 1.

Figure 1:
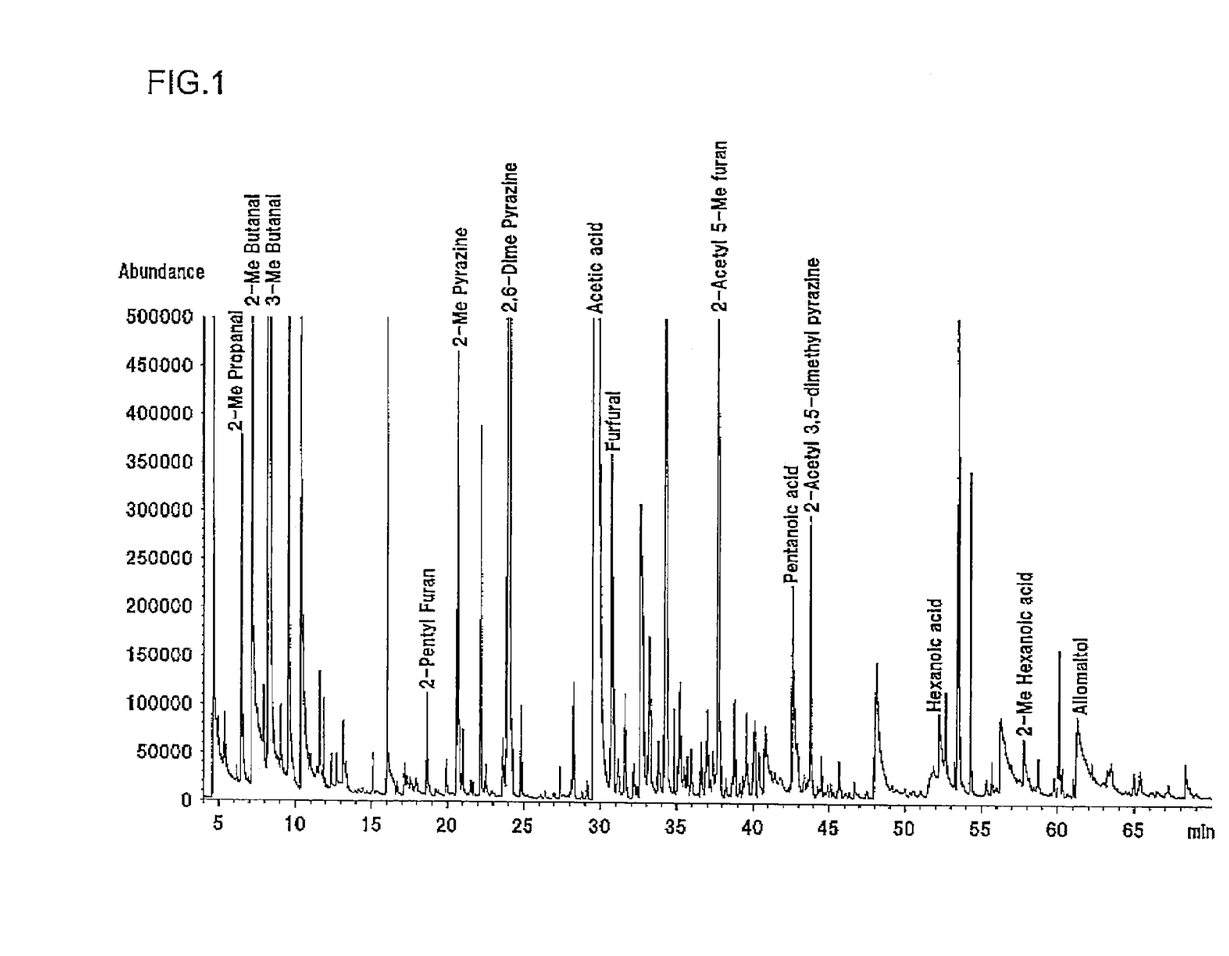
FIG. 1 is a chromatogram showing a GC-MS analysis result of volatile substances generated by reacting dihydroxyacetone with the cutaneous keratin of a human being.

As illustrated in FIG. 1, lower aldehydes, lower fatty acids, furans, pyrans, pyrazines, and others were detected. Out of the low threshold components, in particular, 2,6-dimethylpyrzine showed a high peak abundance.

The same tests were made using 0.1 mL of an aqueous solution of dihydroxyacetone (10% v/v), and a mixture of 10 mg of keratin and 0.1 mL of pure water (wherein the samples were stored for 5 days while heated at 50° C.). In these cases, pyrazines were not detected, either.

Test Example 2

Analysis of Volatile Substances Generated at the Time of the Application of a Self-Tanning Agent, and Evaluation of Contribution of the Substances to Odor Five healthy American women (each Caucasian/white) were requested to cooperate with the present test. The subjects themselves were each requested to apply 0.5 mL of a self-tanning agent (no fragrance was added, dihydroxyacetone concentration: 2% by mass, and erythrulose concentration: 0.5% by mass) to the whole of their left forearms (by their right hands).

Figure 2:
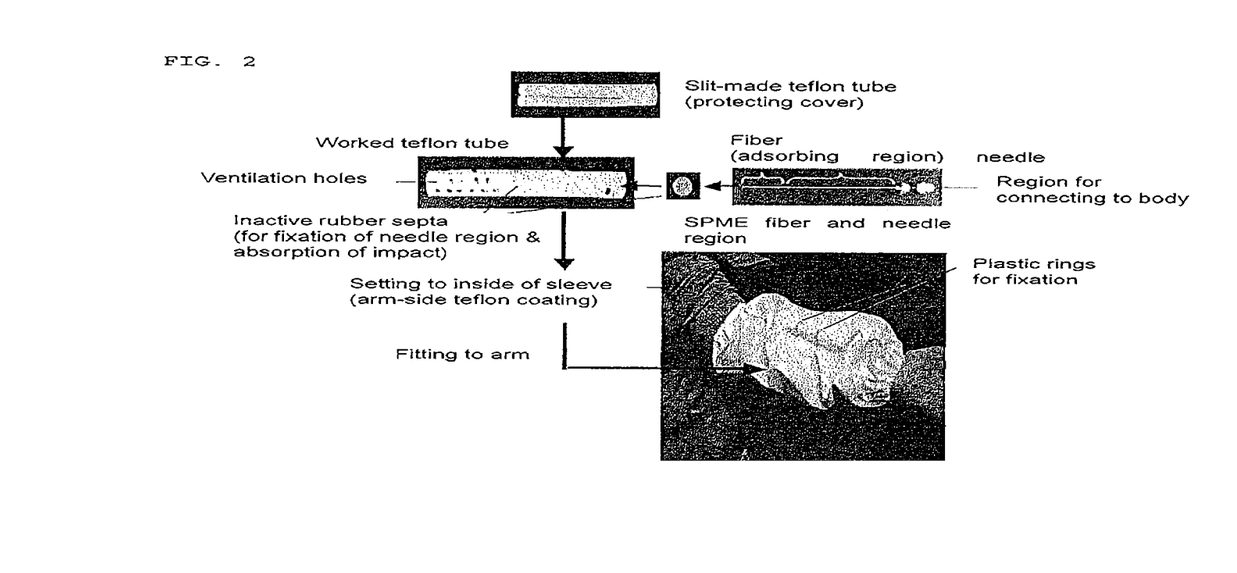
FIG. 2 is a view illustrating a method for collecting volatile substances generated from an arm to which a self-tanning agent was applied.

The resultant reaction odor was collected by a method to which a Solid Phase Micro Extraction (SPME) method was applied. An outline of this method is shown in FIG. 2.

First, many ventilation holes (inside diameter: 4 mm) were made in a tip region (length: 4 cm) of a commercially available Teflon tube (inside diameter: 8 mm, outside diameter: 10 mm, and length: 9 cm). Two circular inactive rubber septa were used to fix a needle part of the SPME inside the Teflon tube. Thereafter, an SPME fiber coated with an adsorbent (the fiber being originally held inside the needle) was pushed out to be exposed. A region (notch) connected to a holder (body) of the SPME was covered with a thin Teflon tube (length: 6 cm) to be protected.

As a sleeve (arm cover), was used a sleeve having a surface covered with Teflon (manufactured by Flon Industry Co., Ltd., diameter: 120 mm, and length: 400 mm). The coated surface was placed on the inside surface (i.e., the arm side), and then the SPME tool was arranged at the center thereof. From the outside, the tool was fixed with two plastic rings. As the SPME fiber, used were a fiber P/N 57335-U (manufactured by Supelco) for 4 hours from a time immediately after the self-tanning agent was used, and then a fiber P/N 57348-U (manufactured by Supelco) for 4 hours. This fiber was used from the 4 hours to 8 hours after the self-tanning agent was used. At the time of exchanging the fibers, the Teflon sleeve was also exchanged with a new one.

(Analysis of Volatile Components Generated from the Arm)

Figure 3:
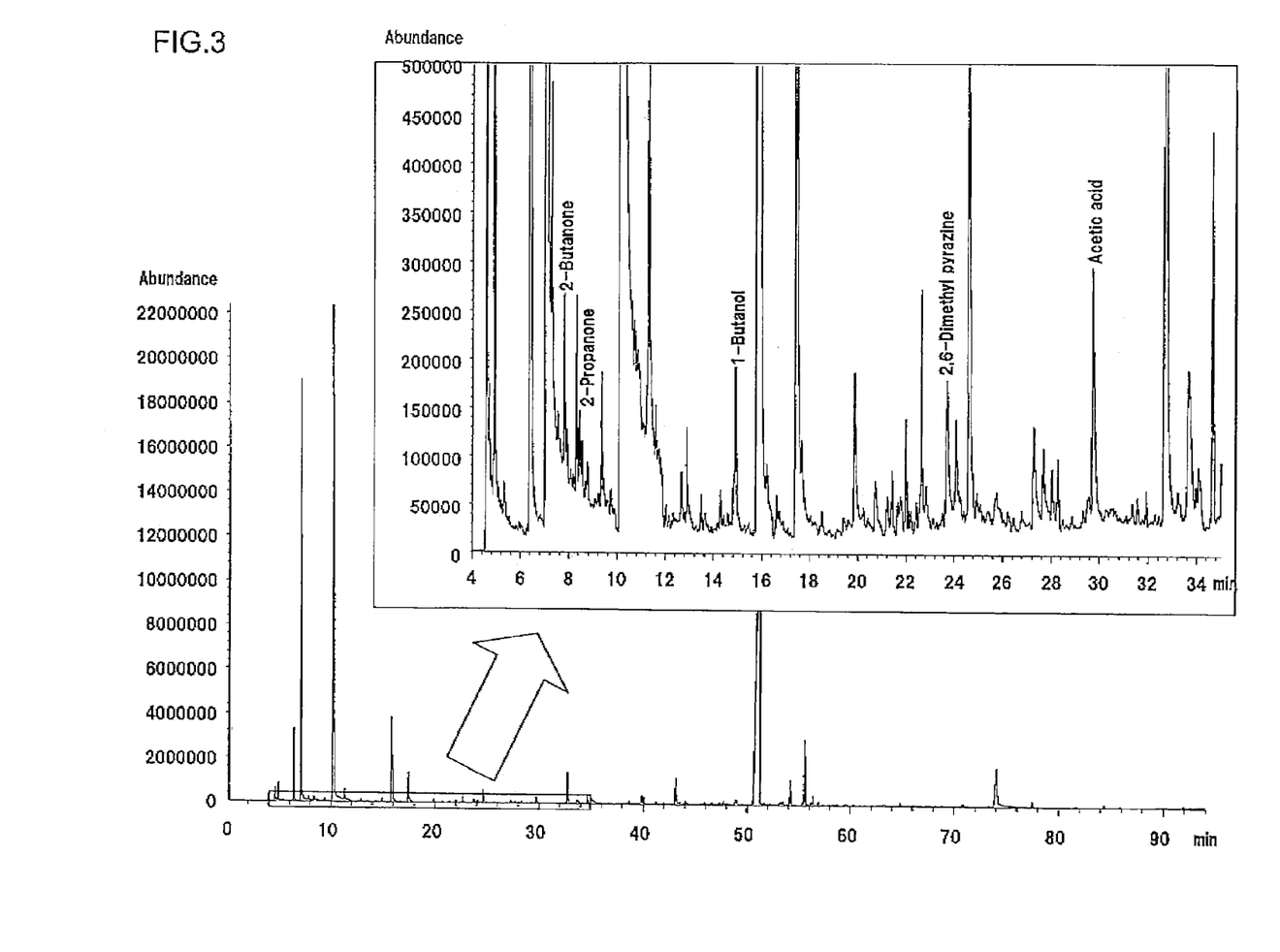
FIG. 3 is a chromatogram showing a GC-MS analysis result of volatile substances generated from an arm to which a self-tanning agent was applied.

An example of results from GC-MS analysis is shown in FIG. 3 (analysis result of components collected from the arm of one of the subjects 4 to 8 hours after the application). Large peaks were made by silicon compounds originating from the SPME fibers. However, when the vicinity of the base line was analyzed in detail, the presence of the following was obvious: lower ketones, a lower alcohol, 2,6-dimethylpirazine, acetic acid, formic acid, and others. The analysis result of volatile substances collected from the arm of each subject 0 to 4 hours after the application was similar to that from the same subject 4 to 8 hours after the application. According to the head space analysis of the arm to which the agent was not applied, 2,6-dimethylpirazine was not detected.

(Evaluation of Contribution of the Substances to Odor)

Odor from the arm of each of the five subjects was subjected to sensory evaluation. For each component that was easily detected directly from the arm after application, the similarity thereof to the reaction odor was evaluated. The obtained results are assembled and shown in Table 1 described below. The evaluation was made by four persons while reagents were used.

[Evaluation Criteria]
A: three persons or more among the four evaluated that the compared odors resembled each other.
B: one or two persons evaluated that the compared odors resembled each other.
C: no person evaluated that the compared odors resembled each other.

TABLE 1

| Component | Similarity of odor |
|---|---|
| Acetaldehyde | C |
| 2-Propanone | C |
| 2-Butanone | C |
| 2-Propanol | C |
| 1-Butanol | C |
| 2,6-Dimethyl pyrazine | A |
| 2-Methyl pyrazine | A |
| 2,5-Dimethyl pyrazine | A |
| Acetic acid | B |
| Formic acid | C |

From Table 1, it is understood that various pyrazine compounds can be used for the evaluation of an odor of a self-tanning agent.

Test Example 3

Relationship Between Volatile Substances Generated when a Self-Tanning Agent is Applied, and Unpleasant Degree The same five healthy American women (each Caucasian/white) who cooperated with Test Example 2 were requested to cooperate with the present test. The subjects themselves were each requested to apply 0.5 mL of a self-tanning agent (no fragrance was added, dihydroxyacetone concentration: 2% by mass, and erythrulose concentration: 0.5% by mass) to the whole of their left forearm (by their right hand). Each subject herself was requested to smell an odor from her arm at respective times of 3 hours, and 6 hours after application. The subject was requested to evaluate the unpleasant degree of the odor in accordance with a criteria described below.

TABLE 2

| Unpleasant degree score | Evaluation criteria |
|---|---|
| 0 | Neutral (Neither Pleasant nor Unpleasant) Odor |
| 1 | Somewhat Unpleasant Odor |
| 2 | Very Unpleasant Odor |

Figure 4:
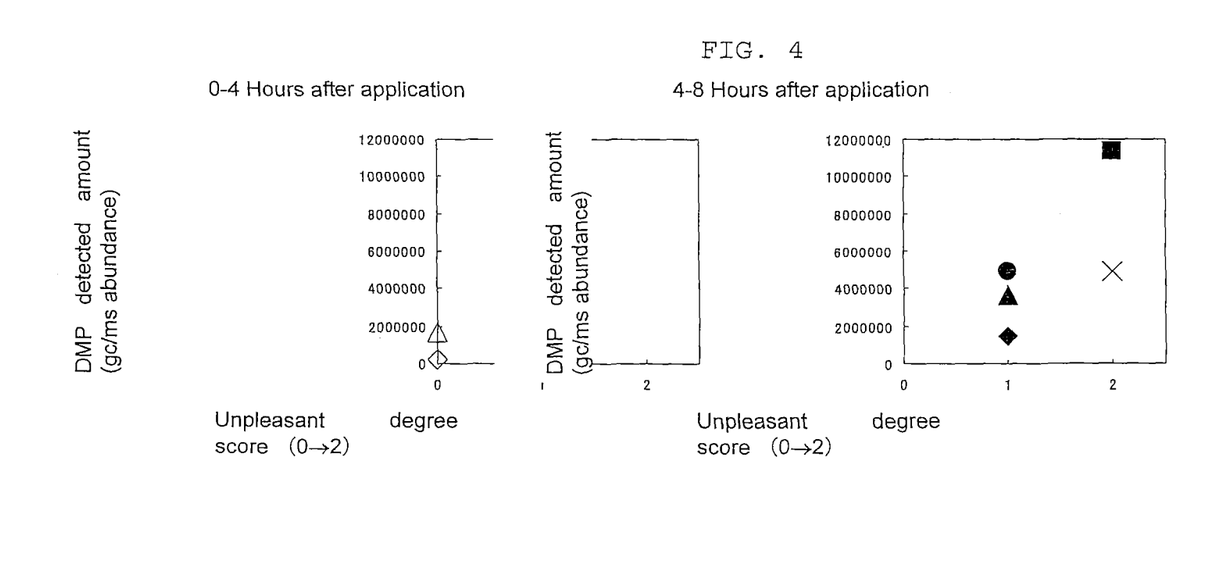
FIG. 4 are graphs showing a relationship between the detected amount of 2,6-dimethylpyrazine from the volatile substances generated from an arm to which a self-tanning agent was applied, and the sensory evaluation of the unpleasant degree of the odor thereof.

From the GC-MS analysis results obtained in Test Example 2, the value of the peak area of dimethylpyrazine detected was obtained. FIG. 4 shows a graphed result of the relationship between the 2,6-dimethylpyrazine detected amount (GC-MS peak area value) and the unpleasant degree of the reaction odor (symbols having the same shape denote the same subject; for example, open circles and filled circles show the results from the same subject, respectively, 0 to 4 hours after application, and 4 to 8 hours after application).

From FIG. 4, it is understood that there is a tendency that as the detected amount of 2,6-dimethylpyrazine increases, the score of the unpleasant degree increases.

What is claimed is:

1. A method for evaluating an odor generated when using a self-tanning agent comprising dihydroxyacetone, wherein at least one compound selected from pyrazine compounds represented by the following general formula (1) is used as an indicator substance:

wherein $R^1$ represents a methyl group, an ethyl group or an acetyl group, and $R^2$, $R^3$ and $R^4$ independently represent a hydrogen atom or a methyl group; which method comprises the following steps (a), (b) and (c):

the step (a) of bringing the stratum corneum of a human being, keratin obtained from the skin of a human being, or a hydrolyzate of any one of the two, into contact with the self-tanning agent comprising dihydroxyacetone, thereby advancing a reaction therebetween, the step (b) of collecting volatile substances generated by the reaction, and the step (c) of measuring the pyrazine compound represented by the general formula (1) that is contained in the collected volatile substances, and evaluating the odor based on this measurement.

2. A method for evaluating an odor generated when using a self-tanning agent comprising dihydroxyacetone, wherein at least one compound selected from pyrazine compounds represented by the following general formula (1) is used as an indicator substance:

wherein $R^1$ represents a methyl group, an ethyl group or an acetyl group, and $R^2$, $R^3$ and $R^4$ independently represent a hydrogen atom or a methyl group; which method comprises the following steps (a), and (c'):

the step (a) of bringing the stratum corneum of a human being, keratin obtained from the skin of a human being, or a hydrolyzate of any one of the two into contact with the self-tanning agent, thereby advancing a reaction therebetween, and the step (c') of smelling volatile substances generated by the reaction, comparing an odor sensed by the smelling with the odor of the pyrazine compound (1) as the indicator substance, and evaluating the sensed odor based on a result of the comparison.

* * * * *